(12) United States Patent
Cutrer et al.

(10) Patent No.: US 8,257,241 B2
(45) Date of Patent: Sep. 4, 2012

(54) BRACHYTHERAPY DEVICE HAVING AN ALIGNMENT AND SEAL ADAPTOR

(75) Inventors: L. Michael Cutrer, Huntington Beach, CA (US); Leigh Spotten, Chatsworth, CA (US); Joseph Wong, South Pasadena, CA (US); Fredrick Winch, Snohomish, WA (US)

(73) Assignee: Portola Medical, Inc., Portola Valley, CA (US)

( * ) Notice: Subject to any disclaimer, the term of this patent is extended or adjusted under 35 U.S.C. 154(b) by 498 days.

(21) Appl. No.: 12/557,040

(22) Filed: Sep. 10, 2009

(65) Prior Publication Data
US 2010/0204536 A1 Aug. 12, 2010

Related U.S. Application Data

(63) Continuation of application No. 11/741,670, filed on Apr. 27, 2007, now abandoned.

(51) Int. Cl.
*A61M 36/12* (2006.01)
(52) U.S. Cl. .......................................................... 600/7
(58) Field of Classification Search .................. 600/1–8; 285/121.6; 606/130, 151; 138/94.3, 94.5, 138/96 R
See application file for complete search history.

(56) References Cited

U.S. PATENT DOCUMENTS

| | | | |
|---|---|---|---|
| 3,114,393 A | 12/1963 | Vlasic | |
| 3,960,393 A | 6/1976 | Hosokawa et al. | |
| 4,423,753 A | 1/1984 | Smith et al. | |
| 4,584,991 A | 4/1986 | Tokita et al. | |
| 4,691,769 A | 9/1987 | Flamm et al. | |
| 4,963,128 A | 10/1990 | Daniel et al. | |
| 4,976,680 A | 12/1990 | Hayman et al. | |
| 5,653,683 A | 8/1997 | D'Andrea | |
| 6,799,605 B1 | 10/2004 | Van Scyoc et al. | |
| 7,357,770 B1* | 4/2008 | Cutrer et al. | 600/3 |
| 2006/0100475 A1* | 5/2006 | White et al. | 600/3 |
| 2006/0100476 A1 | 5/2006 | White et al. | |
| 2007/0142694 A1 | 6/2007 | Cutrer et al. | |
| 2007/0270627 A1* | 11/2007 | Cutrer et al. | 600/7 |
| 2008/0091055 A1 | 4/2008 | Nguyen et al. | |
| 2008/0221384 A1* | 9/2008 | Chi Sing et al. | 600/7 |
| 2008/0269539 A1 | 10/2008 | Cutrer et al. | |

OTHER PUBLICATIONS

U.S. Appl. No. 11/741,670, filed Apr. 27, 2007 (Publication No. 2008/0269539 A1, published Oct. 30, 2008), Office Action, mailed Mar. 10, 2009.

* cited by examiner

*Primary Examiner* — Charles A Marmor, II
*Assistant Examiner* — Catherine E Burk
(74) *Attorney, Agent, or Firm* — Locke Lord LLP

(57) ABSTRACT

A brachytherapy device for treating tissue within a cavity of a body. The device may include a first set of tubes configured to be inserted into the cavity through an opening at the surface of the body. Each of the tubes may have an external end and an interior channel beginning at the external end that is configured to receive radioactive material. The external ends of the tubes may be bundled together. The tubes may be of a length that causes the external ends to be near the opening in the surface of the body while the tubes are in the cavity. A seal may be configured to prevent fluid that originates from the cavity from entering into the external ends of the tubes while they are near the opening in the surface of the body. The seal may include a gasket that is pressed against the external ends of the tubes. The gasket may have openings that align with channels within the external ends of the tubes.

17 Claims, 6 Drawing Sheets

BRACHYTHERAPY DEVICE HAVING AN ALIGNMENT AND SEAL ADAPTOR

CROSS-REFERENCE TO RELATED APPLICATION

This application is a continuation application of U.S. patent application Ser. No. 11/741,670, entitled "Brachytherapy Device Having an Alignment and Seal Adaptor," filed Apr. 27, 2007, the entire content of which is incorporated herein by reference.

BACKGROUND

1. Field

This disclosure relates to brachytherapy devices for treating cancerous tissue surrounding a cavity of a body with radiation.

2. Description of Related Art

Brachytherapy devices may include a set of tubes. Examples are described in U.S. patent application Ser. No. 11/737,028, entitled "Expandable Brachytherapy Device with Constant Radiation Source Spacing," filed Apr. 18, 2007, U.S. patent application Ser. No. 11/379,739, entitled "Brachytherapy Apparatus for Asymmetrical Cavities," filed April 21, 2006, and U.S. patent application Ser. No. 11/305,437, entitled "Brachytherapy Apparatus," filed Dec. 16, 2005, (hereinafter collectively "Prior Brachytherapy Patent Applications"). The entire content of all three of these applications is incorporated herein by reference.

The tubes may be inserted into the cavity of a body through an opening on the surface of the body, such as through an incision or a natural opening. The tubes within the cavity may be expanded. Radioactive material may be inserted within an interior channel in one or more of the tubes and allowed to remain for a prescribed period of time.

The tubes may have external ends that are bundled together. A device known as an afterloader may be coupled to the external ends of the tubes and used to insert radioactive material into one or more of the tubes. Radioactive material may instead be inserted manually.

The external ends of the tubes may be near the opening in the surface of the body, such as protruding slightly beyond the opening. The external ends of the tubes may not be coupled to the afterloader or otherwise accessed for several hours or even days after the tubes are inserted within the cavity. During this period, fluid, such as seroma, may seep from the cavity through spacing between or surrounding the tubes towards the external ends of the tubes. This fluid may enter the interior channels of the tubes and solidify. This may impede the insertion of radioactive material into the interior channels of the tubes and/or its removal.

SUMMARY

A brachytherapy device for treating tissue within a cavity of a body may include a first set of tubes configured to be inserted into the cavity through an opening at the surface of the body. Each of the tubes may have an external end and an interior channel beginning at the external end that is configured to receive radioactive material, the external ends of the tubes being bundled together. The tubes may be of a length that causes the external ends to be near the opening in the surface of the body while the tubes are in the cavity. A seal may be configured to prevent fluid that originates from the cavity from entering into the external ends of the tubes while they are near the opening in the surface of the body.

The external ends of the tubes may lie in substantially the same plane and the seal may include a substantially flat gasket that is pressed against the external ends of the tubes.

The gasket may include a plurality of openings, each of which may be aligned with one of the channels in the tubes so as to allow radioactive material to be inserted into the channel of the tube while preventing fluid that originates from the cavity from entering into the external end of the tube.

The external end of each tube may have a cross-section having an outer perimeter. The opening in the gasket that may be pressed against each external end may not at any point extend beyond the outer perimeter of the external end of the tube.

The brachytherapy device may include an alignment mechanism configured to cause each opening in the gasket that may be pressed against one of the external ends of the tubes to align with the channel in the external end of the tube.

The brachytherapy device may include a cover configured to controllably cover the openings in the gasket.

The cover may be configured to move from a closed position that covers the openings in the gasket to an open position that exposes the openings in the gasket.

The cover may include openings through which radioactive material may be inserted that align with openings in the gasket when the cover is in the open position.

The openings in the cover may not align with the openings in the gasket when the cover is in the closed position.

The cover may include an alignment mechanism that is configured to facilitate alignment of the cover with an afterloader. The alignment mechanism may include a plurality of indentations within a surface of the cover.

The cover may be configured to rotate about an axis while moving between the open and closed positions.

The brachytherapy device may include a fastener configured to fasten the gasket to the tubes.

The brachytherapy device may include a hollow tube surrounded by the ends of the first set of tubes. The gasket may include a central opening. The fastener may include a screw having a shaft that passes through the central opening in the gasket and into the hollow tube.

The brachytherapy device may include a sleeve around the external ends of the tubes.

The brachytherapy device may include a second set of tubes configured to be inserted into the cavity through the opening at the surface of the body along with the first set of tubes. Each of the second set of tubes may have an external end configured to be near the opening in the surface of the body while the first and second sets of tubes are inserted into the cavity. The external ends of the second set of tubes may be bundled together with the external ends of the first set of tubes, and the external ends of the first and second sets of tubes may lie in substantially the same plane. The seal may include a substantially flat gasket that is pressed against the external ends of the first and second sets of tubes.

At least some of the second set of tubes may have an interior channel beginning at the external end of the tube. The gasket may have a plurality of openings, some of which are aligned with channels in the first set of tubes and some of which are aligned with channels in the second set of tubes.

The brachytherapy device may include an alignment mechanism configured to align some of the openings in the gasket with the channels in the first set of tubes. The alignment mechanism may include at least one pin configured to pass through one of the openings in the gasket that aligns with a channel in one of the second sets of tubes and through the corresponding channel in one of the second sets of tubes.

The alignment mechanism may include a plurality of pins, each configured to pass through one of the openings in the gasket that aligns with a channel in one of the second sets of tubes and through the corresponding channel in one of the second sets of tubes.

The second set of tubes may surround the first set of tubes.

A seal may be provided for a brachytherapy device that has tubes configured to be inserted into a cavity through an opening at a surface of a body. The seal may include a substantially flat gasket that is configured to be pressed against the external ends of the tubes. The gasket may have a plurality of openings oriented so as to be aligned with the channels in the tubes when pressed against the external ends of the tubes so as to allow radioactive material to be inserted into the channels of the tubes, while preventing fluid that originates from the cavity from entering into the external ends of the tubes.

A brachytherapy process for treating tissue within a cavity of a body may include inserting a hollow set of tubes into the cavity through an opening at the surface of the body. A cover may be from a closed position that covers entryways to the tubes to an open position that opens the entryway to the tubes. Radioactive material may be inserted into at least one of the tubes while the cover is in the open position. Radioactive material may be removed from the tubes. The cover may be rotated to the closed position.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details that may be apparent or unnecessary may be omitted to save space or for more effective illustration. When the same numeral appears in different drawings, it is intended to refer to the same or like components or steps.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation.

Figure 1:
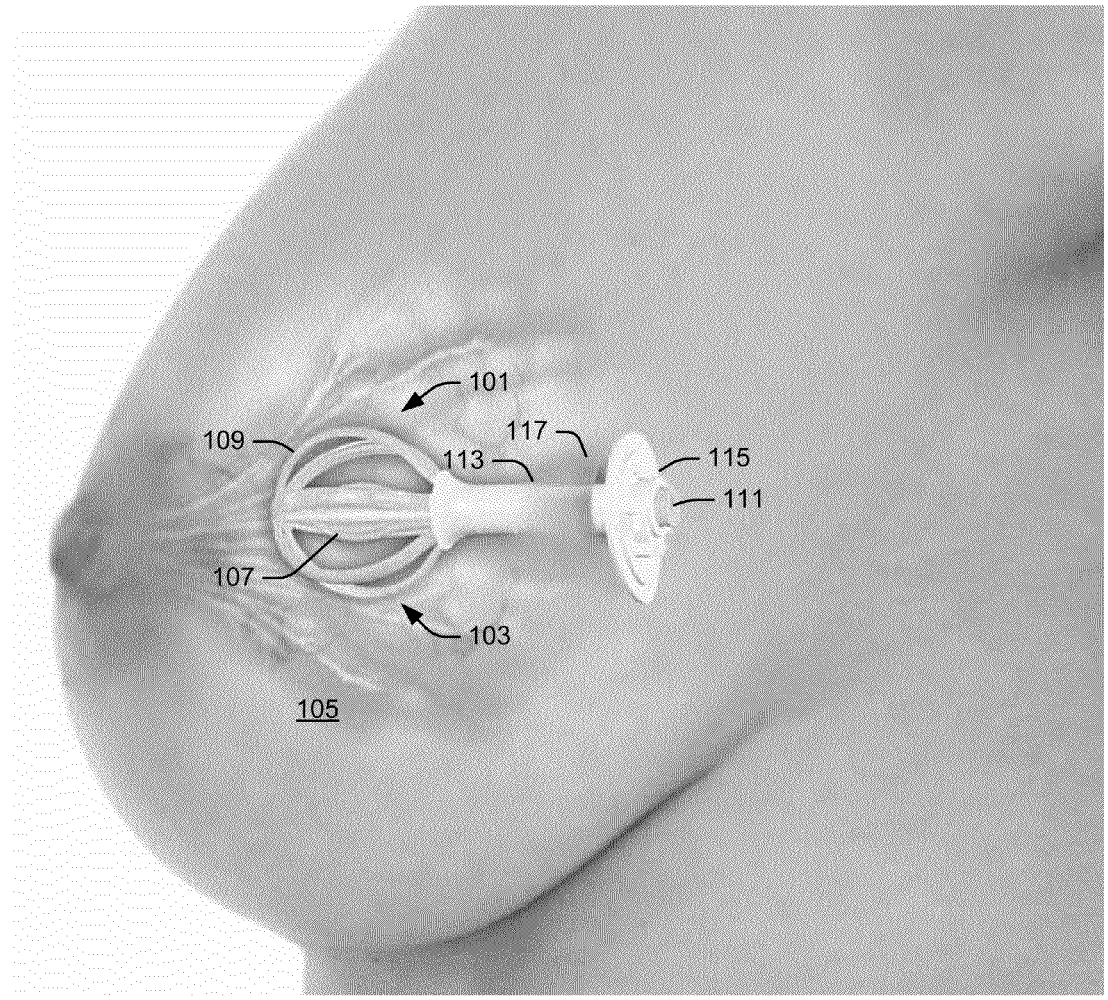
FIG. 1 illustrates a brachytherapy device after being inserted into a breast and expanded.

FIG. 1 illustrates a brachytherapy device after being inserted into a breast and being expanded. As shown in FIG. 1, a brachytherapy device 101 may be inserted into a cavity 103 in a breast 105. The brachytherapy device 101 may include a set of expanded inner tubes 107 and a set of expanded outer tubes 109. The inner tubes 107 and the outer tubes 109 may have external ends 111 that are bundled together. A sleeve 113 may be used to bundle the external ends 111 together. A clamp 115 may be used in addition or instead to bundle the external ends 111 together. The clamp 115 may or may not be integral with the sleeve 113.

The length of the inner tubes 107 and the outer tubes 109 may be such as to cause the external ends 111 to be near a surface 117 of the breast 105, such as slightly protruding from it.

Although having illustrated and discussed one particular type of brachytherapy device, any type of brachytherapy device may be used. More details about the device that has been illustrated and described and processes for causing it to be in the configuration shown in FIG. 1, as well as other types of usable brachytherapy devices, are set forth in the Prior Brachytherapy Patent Applications identified and incorporated by reference above.

The cavity 103 may result from the resection of a tumor. The cavity 103 may in addition or instead be a naturally occurring cavity within the body, such as a cavity within a bladder, vagina, rectum, colon, subglottic region, stomach, bronchial tubes, nasopharynx region, and the like.

Figure 2:
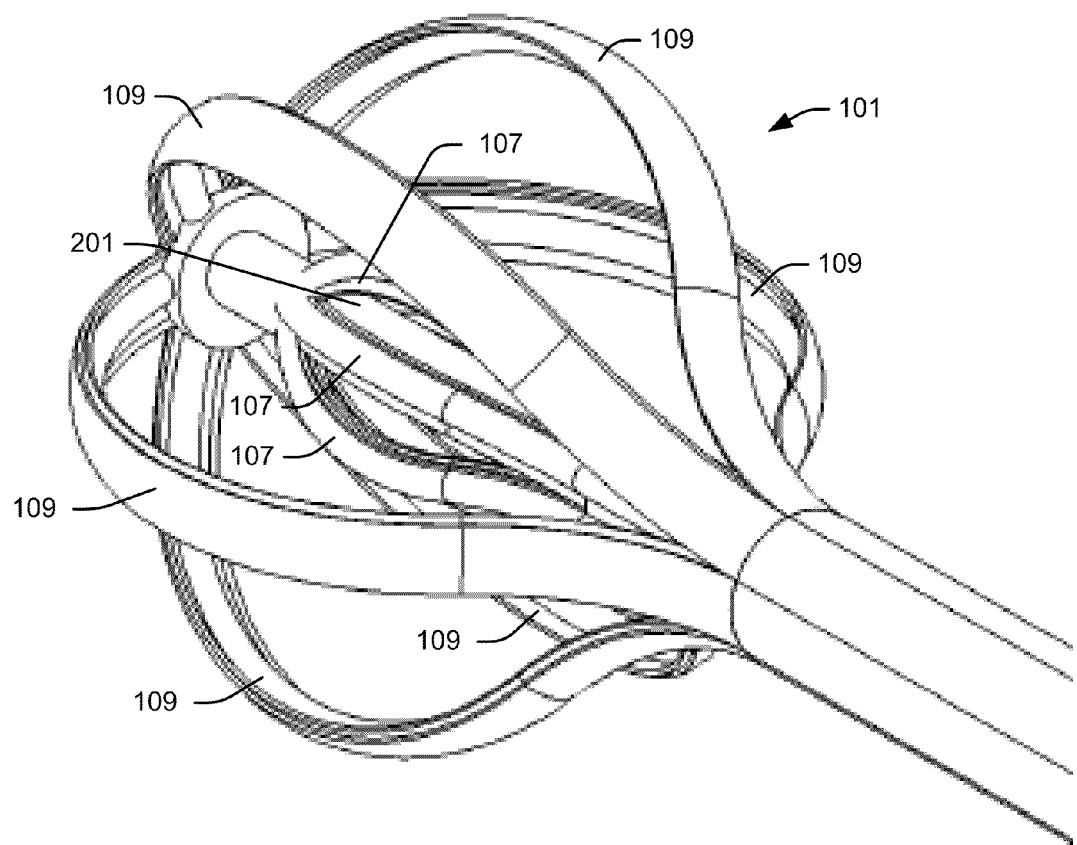
FIG. 2 is an enlarged view of the expanded portion of the brachytherapy device illustrated in FIG. 1.

FIG. 2 is an enlarged view of the expanded portion of the brachytherapy device illustrated in FIG. 1. It reveals details about the inner tubes 107 and the outer tubes 109 shown in FIG. 1. FIG. 2 also illustrates a center tube 201 that may run through the center of the inner tubes 107 and the outer tubes 109.

Figure 3:
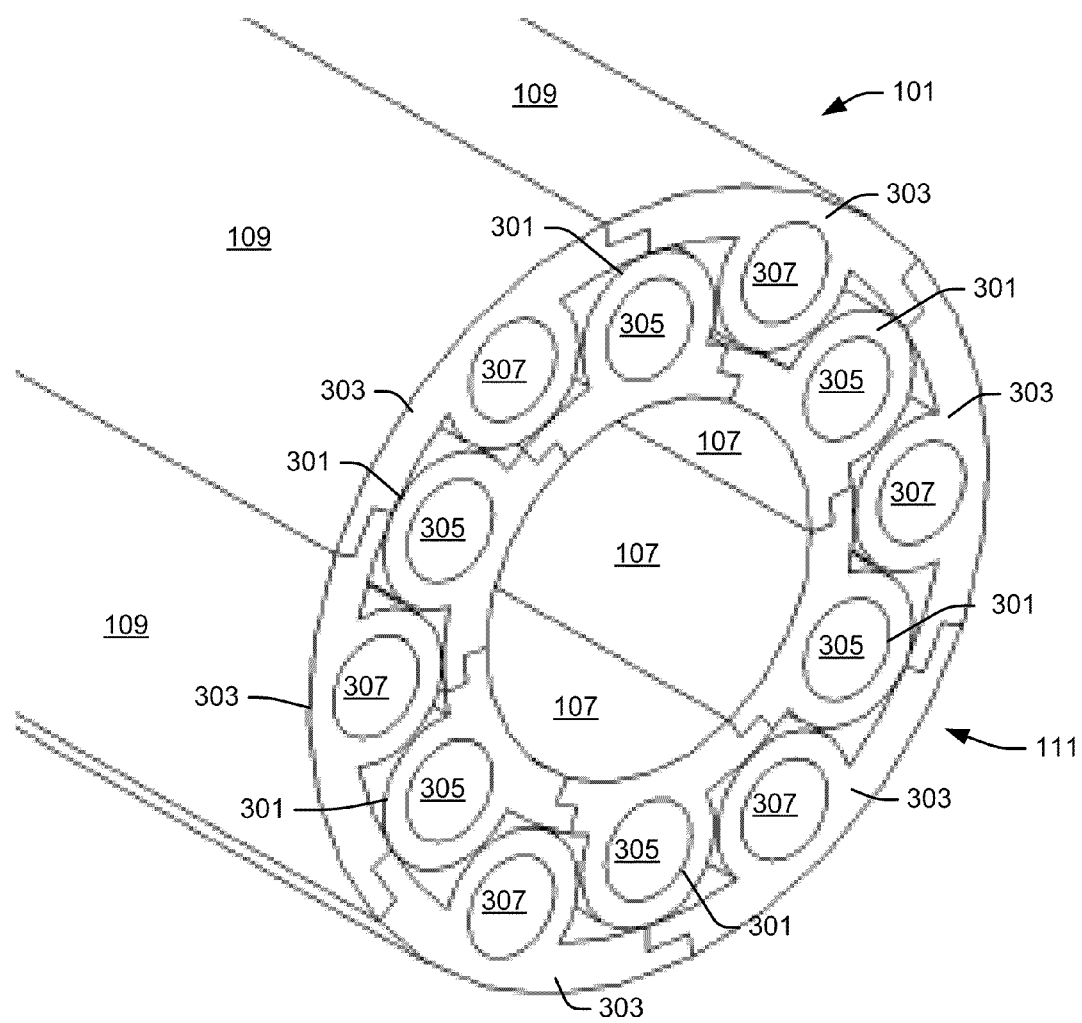
FIG. 3 is an enlarged view of the external end of the brachytherapy device illustrated in FIG. 1 without a center tube.

FIG. 3 is an enlarged view of the external ends 111 of the brachytherapy device 101 illustrated in FIG. 1 without a center tube. As illustrated in FIG. 3, each of the inner tubes 107 may have an external end 301, and each of the outer tubes 109 may have an external end 303. The external ends 301 and 303 may all lie in substantially the same plane.

Each of the inner tubes 107 may have an interior channel 305 beginning at its external end 301 that may or may not be configured to receive radioactive material. Similarly, each of the outer tubes 109 may have an interior channel 307 beginning at its external end 303 that may or may not be configured to receive radioactive material.

During use of the brachytherapy device 101, fluid, such as seroma, may have seeped through spacing between the inner tubes 107 and the outer tubes 109, through or around the center tube 201 and/or between the outer perimeter of the outer tubes 109 and the tissue that surrounds them. Unless stopped, this fluid may seep into the interior channels 305 and/or 307. In turn, this may impede the insertion of radioactive material within one or more of these channels and/or its removal, particularly after the seroma hardens.

Figure 4:
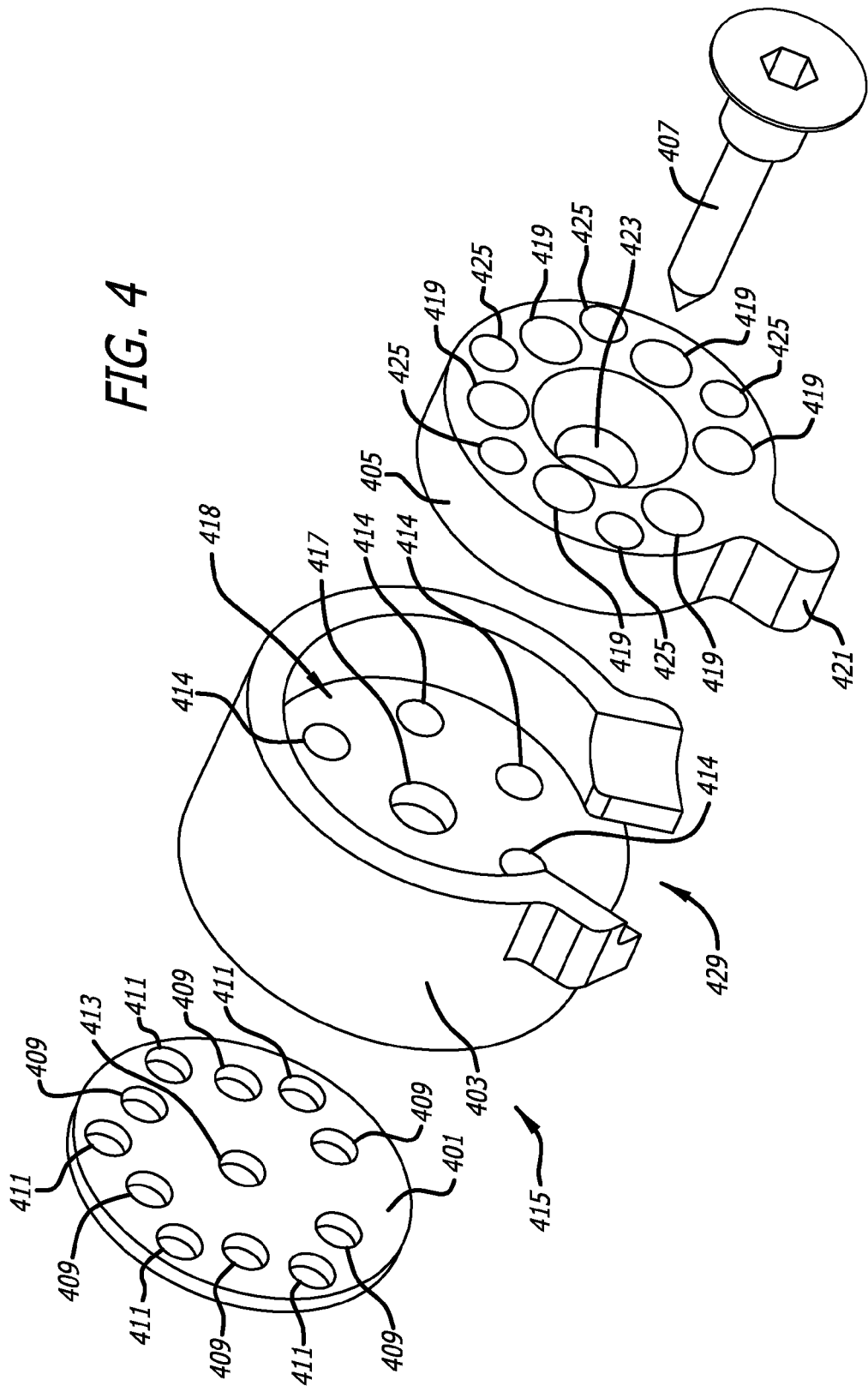
FIG. 4 illustrates an exploded view of a seal and alignment adapter having a gasket, alignment disk, cover and screw.

FIG. 4 illustrates an exploded view of a seal and alignment adaptor. As shown in FIG. 4, the seal and alignment adaptor may include a gasket 401, an alignment disk 403, a cover 405, and a fastener, such as a screw 407.

The gasket 401 may include a set of inner openings 409, a set of outer openings 411, and a central opening 413.

The inner openings 409 may be configured so as to align with the external ends of the channels 305 in the inner tubes 107 when placed against the inner tubes 107. Similarly, the outer openings 411 may be configured to align with the external ends of some of the channels 307 in the outer tubes 109. Similarly, the central opening 413 may be configured to align with the opening in the center tube 201 at the external ends 111.

The openings 409 and/or 411 may be sized so as to permit radioactive material to be inserted into the channels 305 and/or 307, respectively. The openings 409 and/or 411 may also be sized so as not at any point to exceed the perimeter of the cross section of any of the inner tubes 107 and/or the outer tubes 109 at their external ends 111. When so sized and configured, and when the gasket 401 is pressed against the external ends 111 and its openings are aligned with the corresponding channels in the inner tubes 107 and/or the outer tubes 109, radioactive material may be inserted into one or more of these channels. Yet, fluid that may have seeped toward the external ends 111 from within the cavity 103 may be unable to enter any of the channels 305 and/or 307 due to the sealing effect provided by the gasket 401.

The alignment disk 403 may include openings 414, which may be configured to align with the inner openings 409 in the gasket 401. The alignment disk 403 may include a gasket recess 415 sized to house the gasket 401. The alignment disk 403 may include a central opening 417 configured to align with the central opening 413 in the gasket 401.

The alignment disk 403 may include a cover recess 418 configured to house the cover 405. The alignment disk 403 may include an access port 429 that may be configured to provide user access to a tab 421 on the cover 405 when the cover 405 is placed within the cover recess 418 of the alignment disk 403.

The cover 405 may have openings 419 that are configured to align with the openings 414 in the alignment disk 403 and the inner openings 409 in the gasket 401. The cover may include a central opening 423 that is configured to align with the central opening 417 in the alignment disk 403 and the central opening 413 in the gasket 401.

The cover 405 my include an alignment mechanism to facilitate alignment of the cover with an afterloader, such as depressions 425. Depressions 425 may or may not go through the entire thickness of the cover 405.

The screw 407 may be a threaded, self-tapping screw. It may be configured to extend through a central opening 423 in the cover, the central opening 417 in the alignment disk, and the central opening 413 in the gasket, and to then screw into and engage a center bore of the center tube 201 in the brachytherapy device 101. The screw 407 may be tightened so as to ultimately press the gasket 401 against the external ends 111 of the brachytherapy device 101 in an amount that is sufficient to prevent fluid that has seeped toward the external ends 111 from further seeping into the channels 305 of the inner tubes 107 and/or the channels 307 of the outer tubes 109.

In an alternate configuration, a mechanism may be used to hold the gasket 401, the alignment disk 403, and the cover 405 together and to press the gasket 401 against the external ends 111 that does not occupy the central openings 413, 417 and 423. This may leave these central openings available for radioactive material to be inserted therein and into center tube 201.

Figure 5:
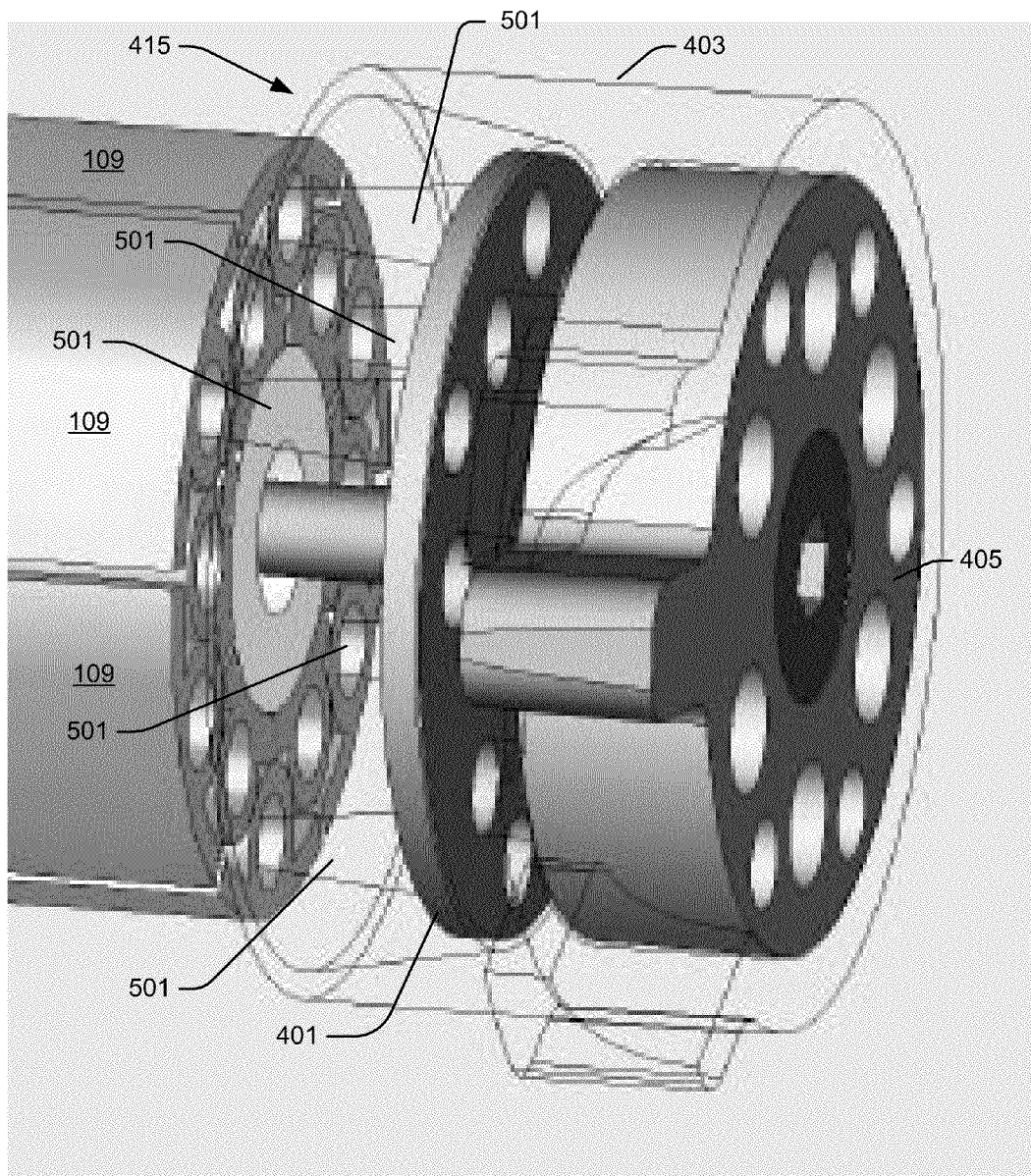
FIG. 5 illustrates an assembled view of the seal and alignment adapter illustrated in FIG. 4 with the alignment disk being transparent and the cover in a closed position.

FIG. 5 illustrates an assembled view of the seal and alignment adaptor illustrated in FIG. 4 with the alignment disk being transparent and the cover in a closed position. As shown in FIG. 5, the alignment disk 403 may include a plurality of pins 501 that protrude from the gasket recess 415 in which the gasket 401 may reside. As shown in FIG. 5, the pins 501 may be configured so as to align with several of the outer openings 411 in the gasket 401 when the gasket 401 is within the gasket recess 415.

The pins 501 may be configured to pass through these outer openings 411 and into some or all of the channels 307 of the outer tubes 109. The pins 501 may have a taper that makes assembly easier. The taper of the pins 501 may be selected so as to cause the pins 501 to fit snugly within the openings 411 of the gasket 401 when the gasket is fully seated within the gasket recess 415 and to fit snugly within the channels 307 of the outer tubes 109 when the external ends 111 of the outer tubes 109 are pressed fully against the gasket 401.

This snug fitting of the pins 501 may contribute to more precise alignment between the channels 305 in the inner tubes 107 and the inner openings 409 in the gasket 401, the openings 414 in the alignment disk 403, and the openings 419 in the cover 405. An alignment mechanism other than the pins 501 may be used in addition or instead. For example, the pins 501 could instead be integral with the gasket 401, in which case there might not be any outer openings 411 in the gasket 401.

Figure 6:
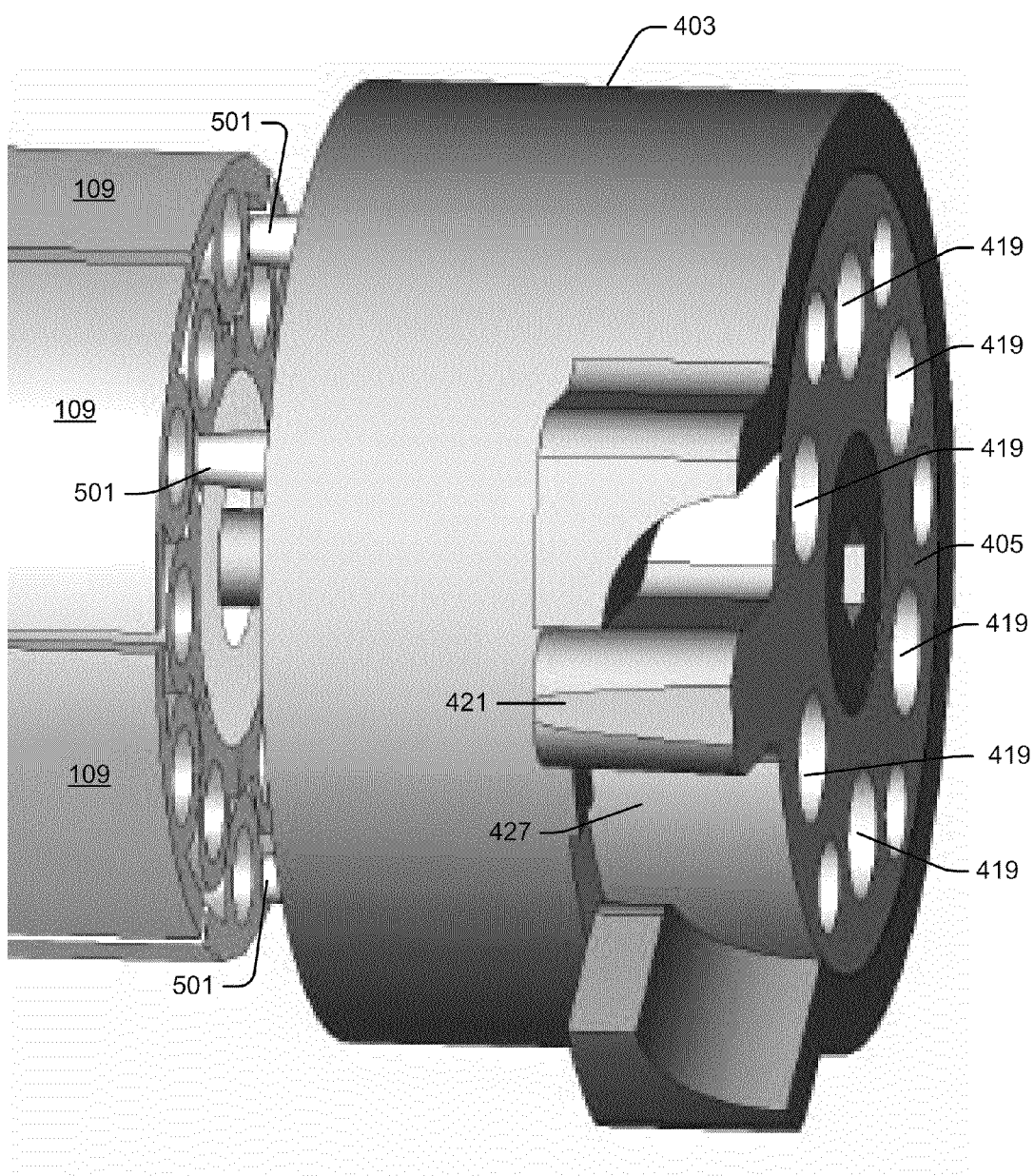
FIG. 6 illustrates an assembled view of the seal and alignment adapter illustrated in FIG. 4 with the cover in a closed position.

FIG. 6 illustrates an assembled view of the seal and alignment adaptor illustrated in FIG. 4 with the cover in a closed position. When the cover 405 is in the position shown in FIG. 6, the tab 421 may be pushed against the uppermost portion of the access port 427. While in this closed position, the openings 419 in the cover 405 may not align with the openings 414 in the alignment disk 403 and the inner openings 409 in the gasket 401. This may effectively block the channels 305 in the inner tubes 107 from being loaded with radioactive material and from otherwise being contaminated. When the cover 405 is rotated counterclockwise by pushing the tab 421 toward the bottom portion of the access port 427 in the alignment disk 403, the openings 419 in the cover 405 may become fully aligned with the openings 414 in the alignment disk 403 and the inner openings 409 in the gasket 401. In this position, the channels 305 in the inner tubes 107 may be loaded with radioactive material inserted through the openings 419 in the cover 405.

The brachytherapy devices that have thus-far been described may be used in a variety of applications.

For example, a tumor may be resected from the breast 105 shown in FIG. 1. A balloon may be inserted into the cavity that is created as a result and inflated. Later, the balloon may be deflated and removed. The cavity may instead be a naturally occurring cavity, such as a cavity in a bladder, vagina, rectum, colon, subglottic region, stomach, bronchial tubes, nasopharynx region, or the like.

The sleeve 113 may be inserted into the cavity. The inner tubes 107 and the outer tubes 109, while in an elongated and collapsed state, may be threaded through the sleeve 113 and into the cavity 103 of the breast 105. The inner tubes 107 and the outer tubes 109 may then be expanded to the positions illustrated in FIGS. 1 and 2. Apparatus for accomplishing this may include any of the devices disclosed in the Prior Brachytherapy Patent Applications identified and incorporated by reference above.

The clamp 115 may be tightened and portions of the inner tubes 107 and the outer tubes 109 that extend substantially beyond the clamp 115 may be cut off. The seal and alignment adaptor illustrated in FIG. 4 may be coupled to the external ends 111 of the brachytherapy device 101 by aligning the pins 501 that protrude from the rear of the alignment disk 403 and that protrude through the gasket 401 with the corresponding channels 307 in the outer tubes 109. The screw 407 may be inserted into the central opening 423 of the cover, the central opening 417 of the alignment disk, the central opening 413 of the gasket, and into the opening of the center tube 201. The screw 407 may be tightened until the gasket 401 is pressed against the external ends 111 of the brachytherapy device 101 with sufficient force to prevent fluid from entering the channels 305 in the inner tubes 107 and/or the channels 307 in the outer tubes 109. The tab 421 may be moved to the closed position, if not already in this position.

When ready for treatment, the tab 421 may be moved to the open position. The alignment depressions 425 may be aligned with an afterloader. The afterloader may be directed to insert radioactive material into one or more of the channels 305 in the inner tubes 107 through the openings 419. The radioactive material may instead be inserted manually.

The radioactive material may include or consist of any type of radioactive material, including material that is itself radioactive, such as radioactive pellets, radioactive seeds, radioactive liquid, and/or radioactive wires, and/or radioactive sources that contain radioactive material, such as encapsulated radioactive pellets or seeds, radioactive particles suspended in liquid, and/or radioactive seeds or pellets embedded in wires of other types of strands. When multiple units of radioactive material are inserted into a channel, the units may be spaced apart. The radioactive material may be left within one or more of the channels 305, following which it may be removed.

In some cases, a unit of radioactive material may be allowed to dwell at different locations within the same channel. In some cases, a unit of radioactive material may be removed from one channel and placed within another channel.

When a radioactive treatment session is complete, the radioactive material may be removed from all of the channels and the cover 405 may be closed by rotating the tab 421 clockwise.

During a subsequent treatment, the cover 405 may again be opened by rotating the tab 421 counterclockwise to the open position and by repeating this or a different treatment regimen.

When all of the radiation treatments have been completed, the clamp 115 may be released and removed. The inner tubes 107 and the outer tubes 109 may be allowed to collapse and elongate. The inner tubes 107 and the outer tubes 109 may be completely removed from the cavity 103, along with the sleeve 113.

The openings 419 in the cover 405, the openings 414 in the alignment disk 403, and the inner openings 409 in the gasket 401 may be of any size. In one embodiment, the openings 419 in the cover 405 may be larger than the openings 414 in the alignment disk 403, which may be larger than the inner openings 409 in the gasket 401, thereby making it easier for the afterloader to insert radioactive material into the channels 305 or for this material to be inserted manually. In one embodiment, the openings 419 in the cover 405 may be approximately 70 thousandths of an inch, the openings 414 in the alignment disk 403 may be approximately 50 thousandths of an inch, the inner openings 409 in the gasket 401 may be slightly larger than approximately 40 thousandths of an inch, and the channels 305 in the inner tubes 107 may be approximately 40 thousandths of an inch. These openings may be tapered from wide to narrow so as to further facilitate the smooth entry of radioactive material from the afterloader or by manual means into the channels 305 in the inner tubes 107.

The components of the seal and alignment adaptor that is shown in FIG. 4 may be made of any material. For example, the gasket may be made of a flexible material, such as silicone, and other components, such as the alignment disk, may be made from an acrylic or a polycarbonate-like material, such as Lexan.

The components, steps, features, objects, benefits and advantages that have been discussed are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages. The components and steps may also be arranged and ordered differently.

For example, the seal that is used may not necessarily be a gasket, as illustrated in FIG. 4. Instead, a powerful clamp may be used that pinches closed the external ends 111 of the channels 305. The seal might in addition or instead be material, such as silicone, that is inserted temporarily into the channels 305.

The bundled external ends 111 may also not necessarily be in a circular arrangement, such as is illustrated in FIG. 3. The bundle may instead have rectangular shape or any other shape.

Although inner and outer tubes have thus-far been illustrated, the brachytherapy device may have only one level of tubes. The number of the inner or outer tubes or of only single-level tubes may be greater or less.

Although radioactive material has thus-far been described as being inserted into the inner tubes, radioactive material may in addition or instead be inserted into one or more of the outer tubes, either at the same time or times as radioactive material is inserted into one or more of the inner tubes, or at one or more different times.

The phrase "means for" when used in a claim embraces the corresponding structures and materials that have been described and their equivalents. Similarly, the phrase "step for" when used in a claim embraces the corresponding acts that have been described and their equivalents. The absence of these phrases means that the claim is not limited to any of the corresponding structures, materials, or acts or to their equivalents.

Nothing that has been stated or illustrated is intended to cause a dedication of any component, step, feature, object, benefit, advantage, or equivalent to the public, regardless of whether it is recited in the claims.

In short, the scope of protection is limited solely by the claims that now follow. That scope is intended to be as broad as is reasonably consistent with the language that is used in the claims and to encompass all structural and functional equivalents.

We claim:

1. A brachytherapy device for treating tissue within a cavity of a body comprising:
   a first set of tubes configured to be inserted into the cavity through an opening at the surface of the body, each of the first set of tubes having an external end and an interior channel beginning at the external end that is configured to receive radioactive material, the external ends of the first set of tubes being bundled together and lying in substantially the same plane and protruding from the opening in the surface of the body while the first set of tubes are in the cavity;
   a seal configured to prevent fluid that originates from the cavity from entering into the external ends of the first set of tubes while they protrude from the opening in the surface of the body, the seal comprising a substantially flat gasket that is pressed against the external ends of the first set of tubes, and the gasket comprising a plurality of openings, each of which is aligned with one of the channels in the first set of tubes so as to allow radioactive material to be inserted into the channels of the first set of tubes while preventing fluid that originates from the cavity from entering into the external ends of the first set of tubes;
   a fastener configured to fasten the gasket to the tubes; and
   a hollow tube surrounded by the ends of the first set of tubes and running substantially parallel to the full length of the first set of tubes, wherein the gasket includes a central opening and the fastener includes a screw having a shaft that passes through the central opening in the gasket and into the hollow tube.

2. The brachytherapy device of claim 1 wherein the external end of each of the first set of tubes has a cross-section having an outer perimeter and wherein the opening in the gasket that is pressed against each external end does not at any point extend beyond the outer perimeter of the external end of the tube.

3. The brachytherapy device of claim 2 further comprising an alignment mechanism configured to cause each opening in the gasket that is pressed against one of the external ends of the first set of tubes to align with the channel in the external end of the tube.

4. The brachytherapy device of claim 1 further comprising a cover configured to cover the openings in the gasket.

5. The brachytherapy device of claim 4 wherein the cover is configured to move from a closed position that covers the openings in the gasket to an open position that exposes the openings in the gasket.

6. The brachytherapy device of claim 5 wherein the cover includes openings through which radioactive material may be inserted that align with openings in the gasket when the cover is in the open position.

7. The brachytherapy device of claim 6 wherein the openings in the cover do not align with the openings in the gasket when the cover is in the closed position.

8. The brachytherapy device of claim 6 wherein the cover includes an alignment mechanism that is configured to facilitate alignment of the cover with an afterloader.

9. The brachytherapy device of claim 8 wherein the alignment mechanism includes a plurality of indentations within a surface of the cover.

10. The brachytherapy device of claim 5 wherein the cover is configured to rotate about an axis while moving between the open and closed positions.

11. The brachytherapy device of claim 1 further comprising a sleeve around the external ends of the first set of tubes.

12. The brachytherapy device of claim 1 further comprising a second set of tubes configured to be inserted into the cavity through the opening at the surface of the body along with the first set of tubes, each of the second set of tubes having an external end configured to be near the opening in the surface of the body while the first and second sets of tubes are inserted into the cavity, the external ends of the second set of tubes being bundled together with the external ends of the first set of tubes, wherein the external ends of the first and second sets of tubes lie in substantially the same plane and wherein the seal includes a substantially flat gasket that is pressed against the external ends of the first and second sets of tubes.

13. The brachytherapy device of claim 12 wherein at least some of the second set of tubes have an interior channel beginning at the external end of the corresponding tube, and wherein the gasket has a plurality of openings, some of which are aligned with channels in the first set of tubes and some of which are aligned with channels in the second set of tubes.

14. The brachytherapy device of claim 13 further including an alignment mechanism configured to align some of the openings in the gasket with the channels in the first set of tubes, the alignment mechanism including at least one pin configured to pass through one of the openings in the gasket that aligns with a channel in one of the second set of tubes and through the corresponding channel in one of the second set of tubes.

15. The brachytherapy device of claim 14 wherein the alignment mechanism includes a plurality of pins, each configured to pass through one of the openings in the gasket that aligns with a channel in one of the second set of tubes and through the corresponding channel in one of the second set of tubes.

16. The brachytherapy device of claim 12 wherein the second set of tubes surround the first set of tubes.

17. A brachytherapy process for treating tissue within a cavity of a body comprising in the order recited:
inserting a hollow set of tubes into the cavity through an opening at the surface of the body so as to leave the ends of the tubes protruding from the surface of the body, each of the tubes having an interior channel beginning at the end that is configured to receive radioactive material;
attaching a seal to the ends of the tubes for preventing fluid from entering into the ends of the tubes, the seal comprising a gasket and a cover, and the gasket comprising a plurality of openings each of which is aligned with one of the channels in the tubes;
rotating the cover from a closed position that covers entryways to the tubes to an open position that opens the entryway to the tubes;
inserting radioactive material into at least one of the tubes while the cover is in the open position;
removing the radioactive material from the tubes; and
rotating the cover to the closed position.

* * * * *